US012697108B2

(12) United States Patent
Martin et al.

(10) Patent No.: US 12,697,108 B2
(45) Date of Patent: *Aug. 4, 2026

(54) SURGICAL RETRACTOR SYSTEM AND SNAP JOINT CLAMP

(71) Applicant: Thompson Surgical Instruments, Inc., Traverse City, MI (US)

(72) Inventors: Chris Martin, Empire, MI (US); Steve Nowak, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/958,558

(22) Filed: Nov. 25, 2024

(65) Prior Publication Data

US 2025/0082317 A1     Mar. 13, 2025

Related U.S. Application Data

(63) Continuation of application No. 17/717,891, filed on Apr. 11, 2022, now Pat. No. 12,150,634.

(51) Int. Cl.
| | |
|---|---|
| *A61B 17/02* | (2006.01) |
| *A61B 17/00* | (2006.01) |
| *A61B 90/50* | (2016.01) |

(52) U.S. Cl.
CPC .......... *A61B 17/0206* (2013.01); *A61B 90/50* (2016.02); *A61B 2017/00477* (2013.01)

(58) Field of Classification Search
CPC ................ A61B 17/0206; A61B 90/50; A61B 2017/00477
See application file for complete search history.

(56) References Cited

U.S. PATENT DOCUMENTS

| | | | | |
|---|---|---|---|---|
| 5,020,195 | A | 6/1991 | LeVahn | |
| 5,242,240 | A | 9/1993 | Gorham | |
| 5,888,197 | A | 3/1999 | Mulac | |
| 5,897,087 | A | * 4/1999 | Farley .................. | A61B 90/50 |
| | | | | 248/316.2 |
| 6,736,775 | B2 | 5/2004 | Phillips | |
| 7,294,107 | B2 | 11/2007 | Simon | |
| 7,749,163 | B2 | 7/2010 | Mulac | |
| 9,084,631 | B2 | 7/2015 | Mullaney | |
| 2002/0177754 | A1 | 11/2002 | Phillips | |

(Continued)

OTHER PUBLICATIONS

International Search Report and Written Opinion for PCT/US2023/016892, mailed Jul. 5, 2023, 7 pages.

*Primary Examiner* — Diana Jones
(74) *Attorney, Agent, or Firm* — McAndrews, Held & Malloy, Ltd.

(57)     ABSTRACT

A joint clamp for a surgical retractor system includes a knob, a lower clamp, one or more upper clamps between the lower clamp and the knob, and a bolt that passes through the one or more upper clamps. The lower clamp includes a spring, an upper portion, a lower portion pivotally coupled to the upper portion, and a clamping passage that passes laterally through the upper and lower portions of the lower clamp. The bolt includes a bolt upper portion coupled to the knob and a lower portion secured to the upper portion of the lower clamp. The spring exerts a biasing force on the lower portion of the lower clamp that pivots threads of the lower clamp toward the upper portion of the lower clamp.

20 Claims, 17 Drawing Sheets

(56)  References Cited

U.S. PATENT DOCUMENTS

| | | |
|---|---|---|
| 2005/0080321 A1 | 4/2005 | Bjork |
| 2007/0213597 A1 | 9/2007 | Wooster |
| 2009/0088751 A1* | 4/2009 | Mullaney ........... A61B 17/6466 |
| | | 606/54 |
| 2012/0004659 A1* | 1/2012 | Miller ................... A61B 17/60 |
| | | 606/54 |
| 2014/0378774 A1 | 12/2014 | Wooster |
| 2021/0330420 A1 | 10/2021 | Nowak |

* cited by examiner

Cross Section A-A

Cross Section B-B

Cross Section C-C

Cross Section D-D

Cross Section A-A

Cross Section B-B

Cross Section C-C

Cross Section D-D

SURGICAL RETRACTOR SYSTEM AND SNAP JOINT CLAMP

CROSS-REFERENCE TO RELATED APPLICATIONS

This application claims priority to U.S. patent application Ser. No. 17/717,891, filed Apr. 11, 2022, the disclosure of which is incorporated herein by reference in its entirety.

BACKGROUND OF THE INVENTION

The present invention relates to retractor systems used during surgical procedures.

During surgical procedures, a surgeon typically makes an incision in a patient to access a site of interest for the particular surgical procedure. To maintain clear access to the site of interest, a surgical retractor system is typically utilized. A surgical retractor system typically includes a rail clamp, a frame connected to the rail clamp by a joint clamp, and retractor blades that are connected to the frame by additional joint clamps. The rail clamp is commonly secured to an operating table and provides a fixed and sturdy support for the frame and the retractor blades. Each of the components in a typical surgical retractor system is conventionally made of stainless steel. Other materials such as aluminum and titanium have also been used.

Limitations and disadvantages of conventional and traditional approaches should become apparent to one of skill in the art, through comparison of such systems with aspects of the embodiments set forth in the remainder of the present disclosure.

BRIEF SUMMARY OF THE INVENTION

Surgical retractor systems and joint clamps for such surgical retractor systems are shown in and/or described in at least one figure of the present disclosure. Such surgical retractor systems, joint clamps, and/or other aspects of the present disclosure are set forth more completely in the claims. Advantages, aspects, novel features, as well as, details of illustrated embodiments will be more fully understood from the following description and figures.

DETAILED DESCRIPTION OF THE INVENTION

Figure 1:
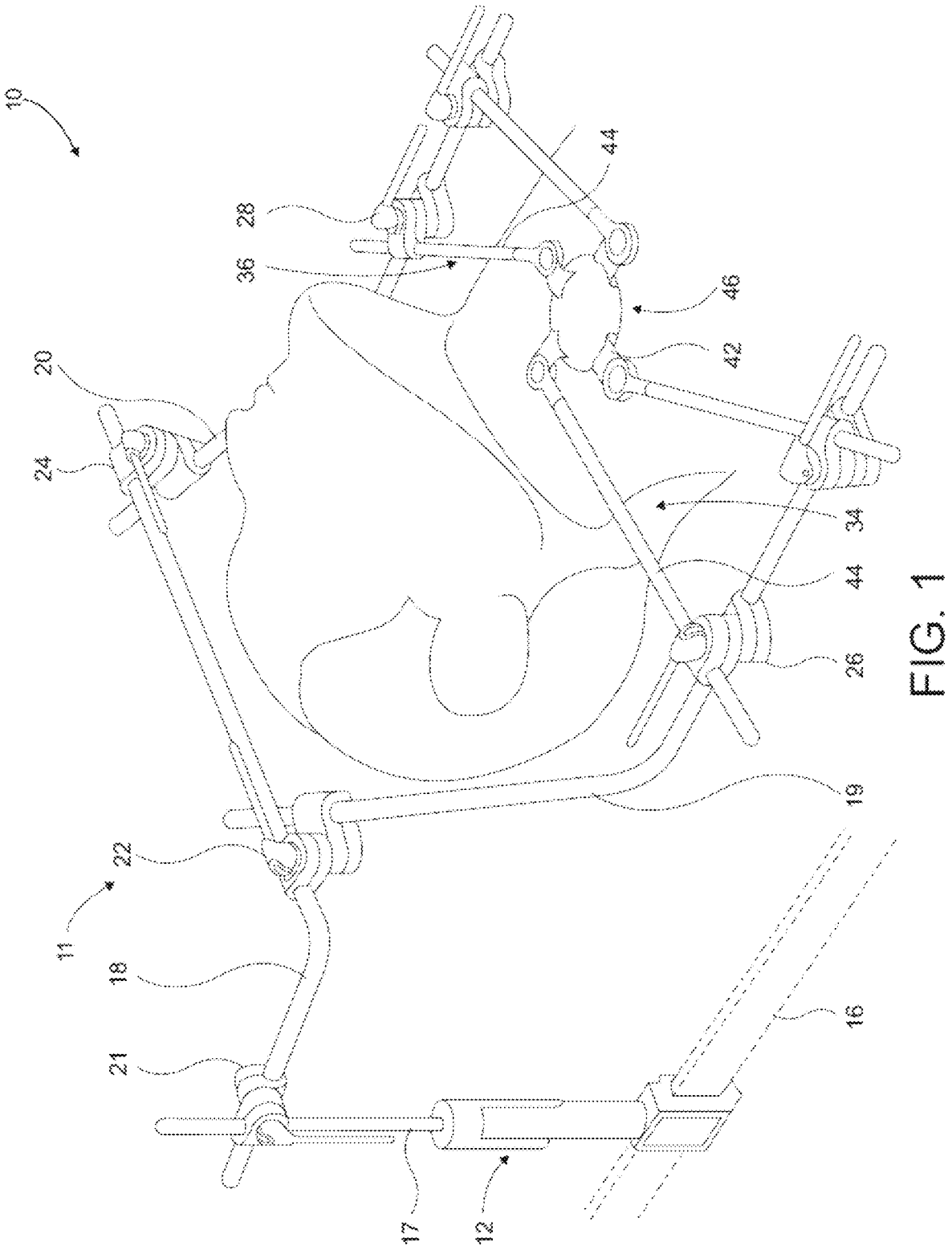
FIG. 1 is a perspective view of a surgical retractor system having joint clamps per one or more embodiments described herein.

Various aspects of the present disclosure are presented by way of example. Such examples are non-limiting, and thus the scope of various aspects of the present disclosure are not necessarily limited by any particular characteristics of the provided examples. In the following, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and Z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like specify the presence of stated features, integers, steps, operations, elements, and/or components, but do not preclude the presence or addition of one or more other features, integers, steps, operations, elements, components, and/or groups thereof.

Although the terms first, second, etc. may be used herein to describe various elements, these elements should not be limited by these terms. These terms are only used to distinguish one element from another element. Thus, for example, a first element, a first component, or a first section could be termed a second element, a second component, or a second section without departing from the teachings of the present disclosure. Similarly, various spatial terms, such as "upper," "lower," "side," and the like, may be used in distinguishing one element from another element in a relative manner. However, components may be oriented in different manners without departing from the teachings of the present disclosure. For example, a component may be turned sideways so that its "top" surface faces horizontally and its "side" surface faces vertically.

In the drawings, various dimensions (e.g., thicknesses, widths, lengths, etc.) may be exaggerated for illustrative clarity. Additionally, like reference numbers are utilized to refer to like elements through the discussions of various examples.

Referring now to FIG. 1, a surgical retractor system 10 may include a frame 11. The frame 11 may secure retractor blades 34, 36 to a surgical table 16 to eliminate or reduce movement of the retractor blades 34, 36 relative to the surgical table 16 and a patient on the surgical table 16. To this end, the frame 11 may include adjustable rail clamps 12, and various frame members such as posts 17, cross bars 18, extension arms 19, 20. The frame 11 may further include multi-directional joint clamps 21, 22, 24, 26, 28 (hereafter "joint clamp or joint clamps"). A first adjustable rail clamp 12 may be secured to one side of the surgical table 16. A second adjustable rail clamp (not shown) may be secured to an opposite side of the surgical table 16 for increased stability. A post 17 may extend vertically from the rail clamp 12 to provide support for a cross bar 18 which in turn provides support for a pair of extension arms 19, 20. The cross bar 18 may be secured to the post 17 by a joint clamp 21. The extension arms 19, 20 may be respectively secured to the cross bar 18 by a pair of joint clamps 22, 24. In some configurations, the extension arms 19, 20 may be secured directly to the post 17 by a joint clamp, thus eliminating the cross bar 18 in certain circumstances.

Additional joint clamps 26, 28 may be disposed along the extension arms 19, 20. The joint clamps 26, 28 may secure retractor blades 34, 36 to the extension arms 19, 20. Each retractor blade 34, 36 may include a blade portion 42 and a retractor handle 44. The blade portion 42 may extend downwardly into the incision 46 made by the surgeon and may retract anatomical features to improve the surgeon's access via the incision 46 to other anatomical features of the patient.

Figure 2:
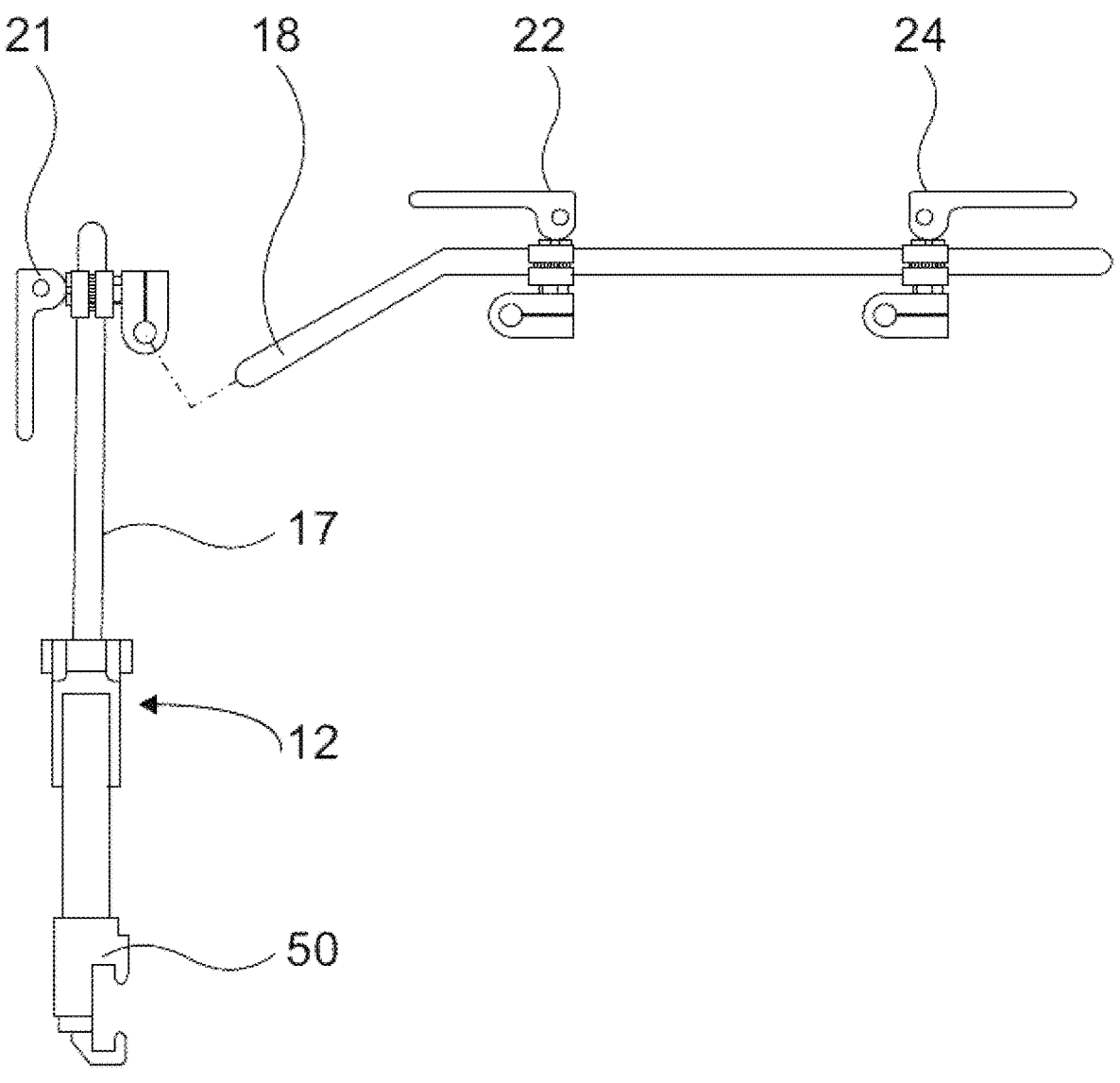
FIG. 2 is an elevated view of the rail clamp, joint clamps, and cross bar of the surgical retractor system shown in FIG. 1.

FIG. 2 provides an another view of the rail clamp 12 and the cross bar 18 of FIG. 1. The rail clamp 12 may include a clamp 50 that may be secured to the surgical table 16 of FIG. 1. The joint clamp 21 is shown at an upper distal end of the post 17. However, the joint clamp 21 may be positioned anywhere along the post 17 so as to position the cross bar 18 at an appropriate height for a surgical procedure. FIG. 2 further shows the joint clamps 22, 24 at respective positions along the cross bar 18. The joint clamps 22 and 24 may be identical to each other or may differ depending on the intended use of each of the clamps 22, 24. Additionally, the joint clamps 22, 24 may each be the same as or differ from the joint clamp 21 on the post 17.

Figures 3A, 3B, 3C, 3D:
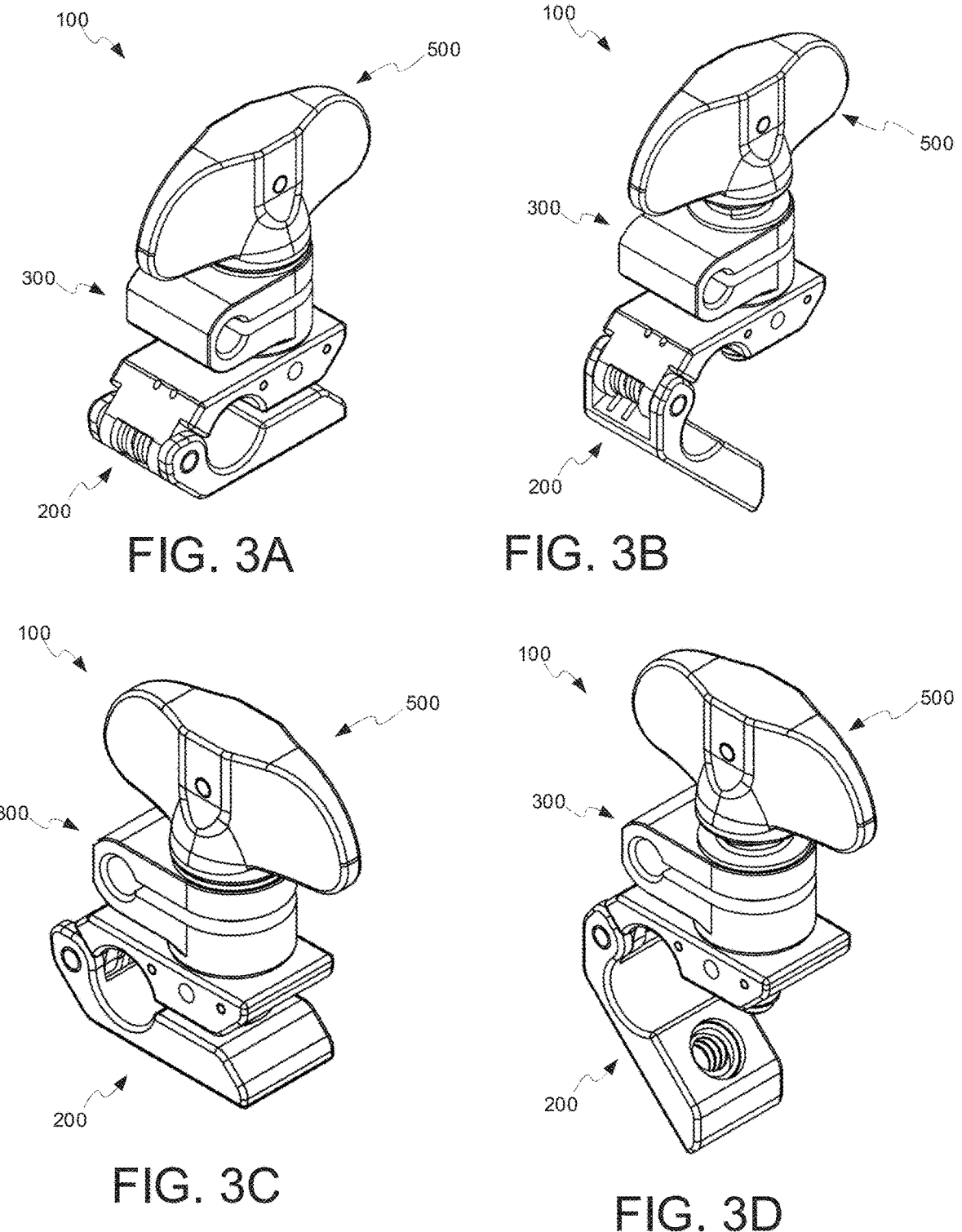
FIGS. 3A-3N provide various views of a first embodiment of a joint clamp for the retractor system shown in FIG. 1.
Figure 3E:
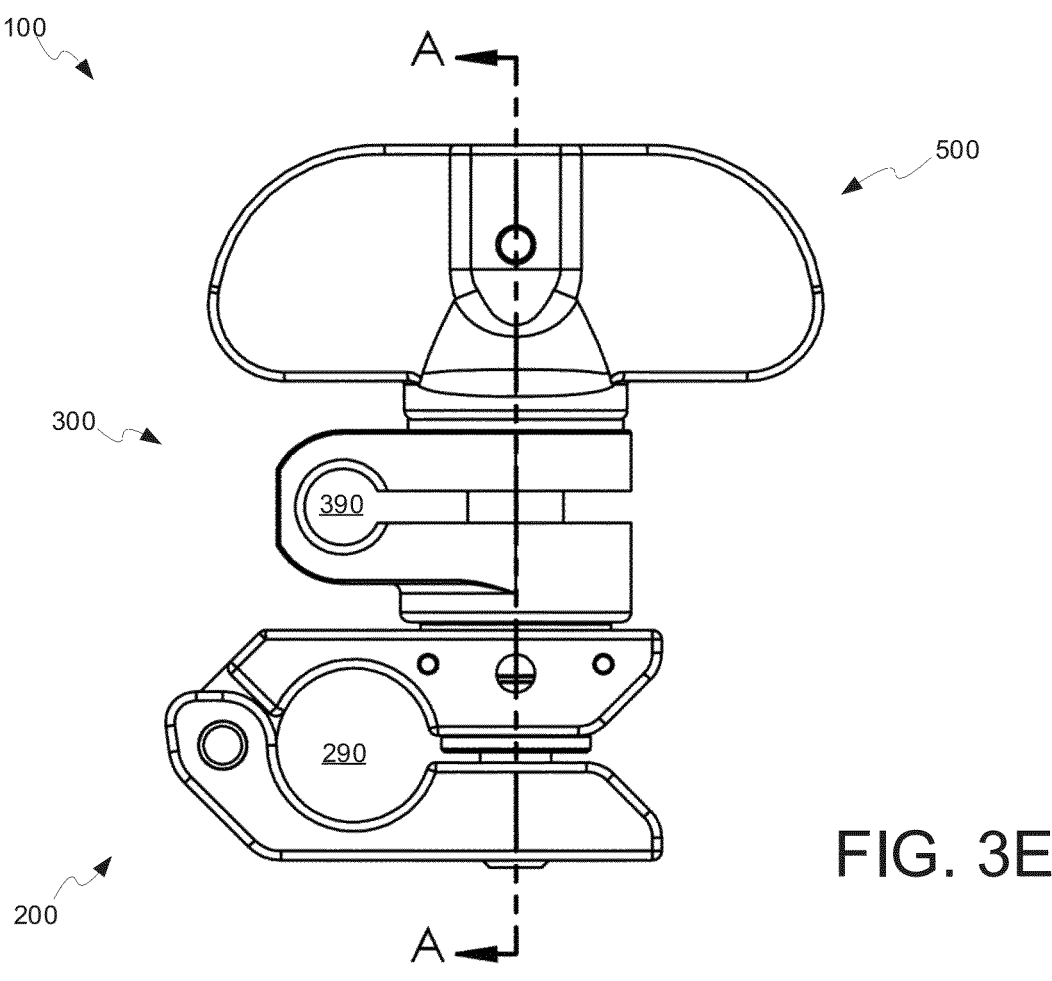
Figure 3F:
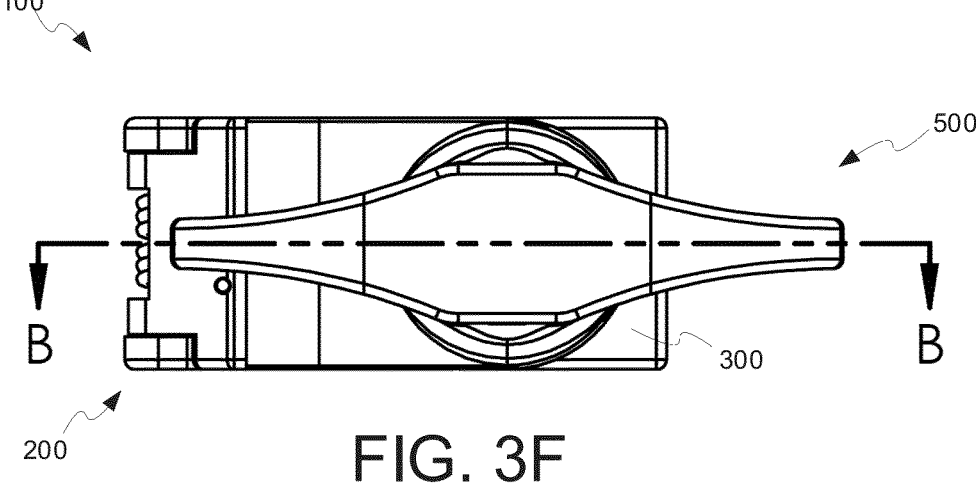
Figure 3G:
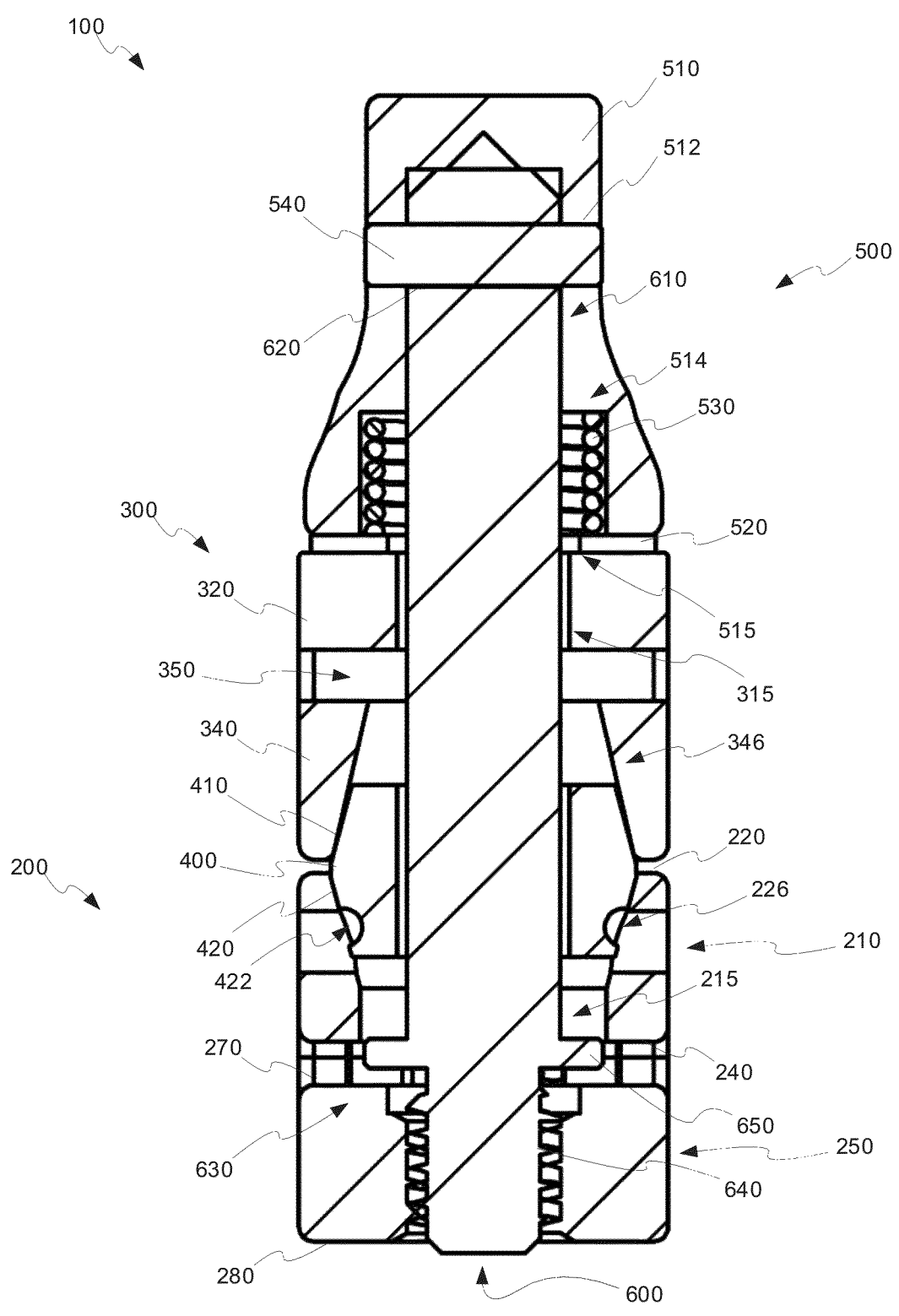
Figure 3H:
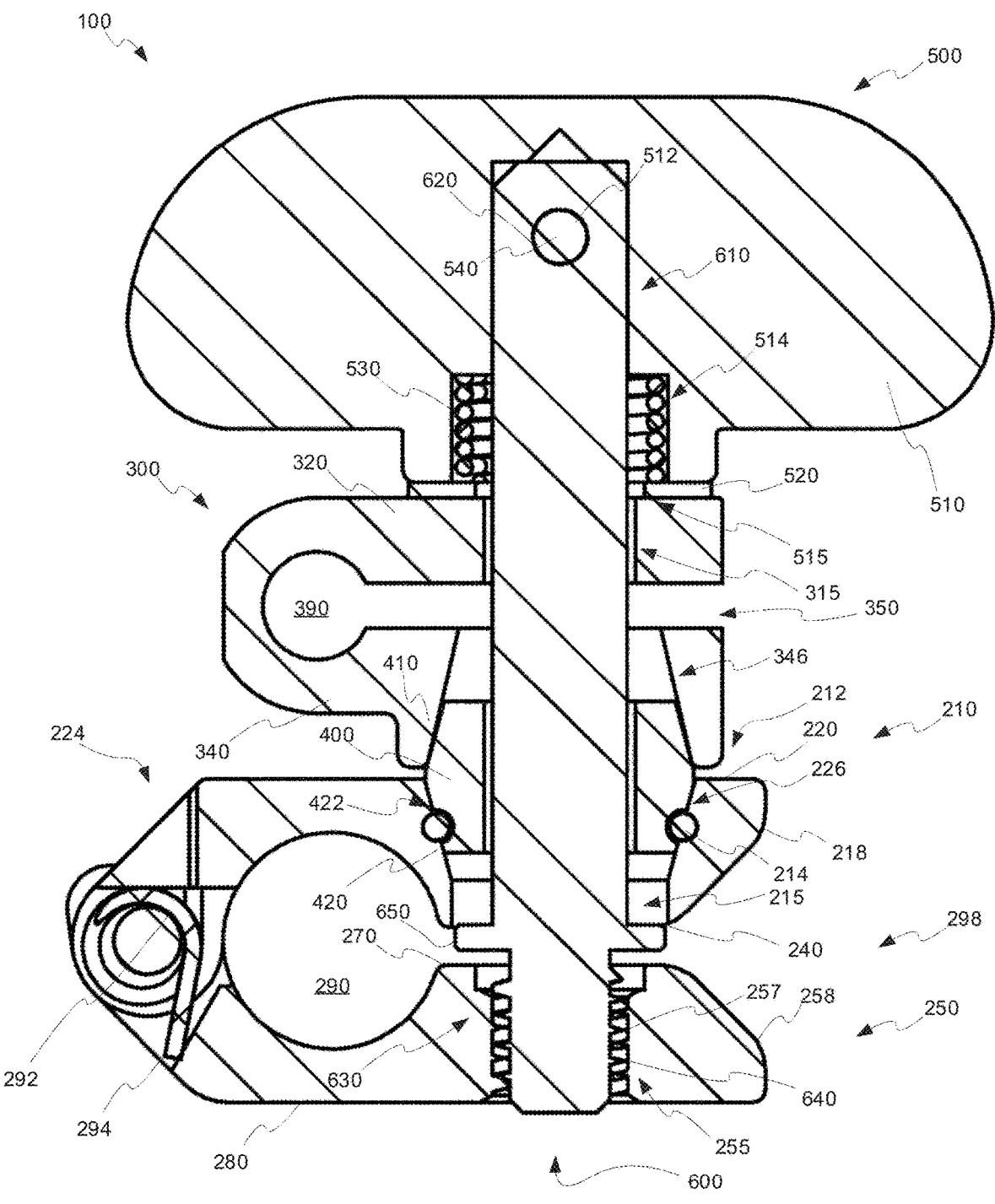
Figures 3I, 3J:
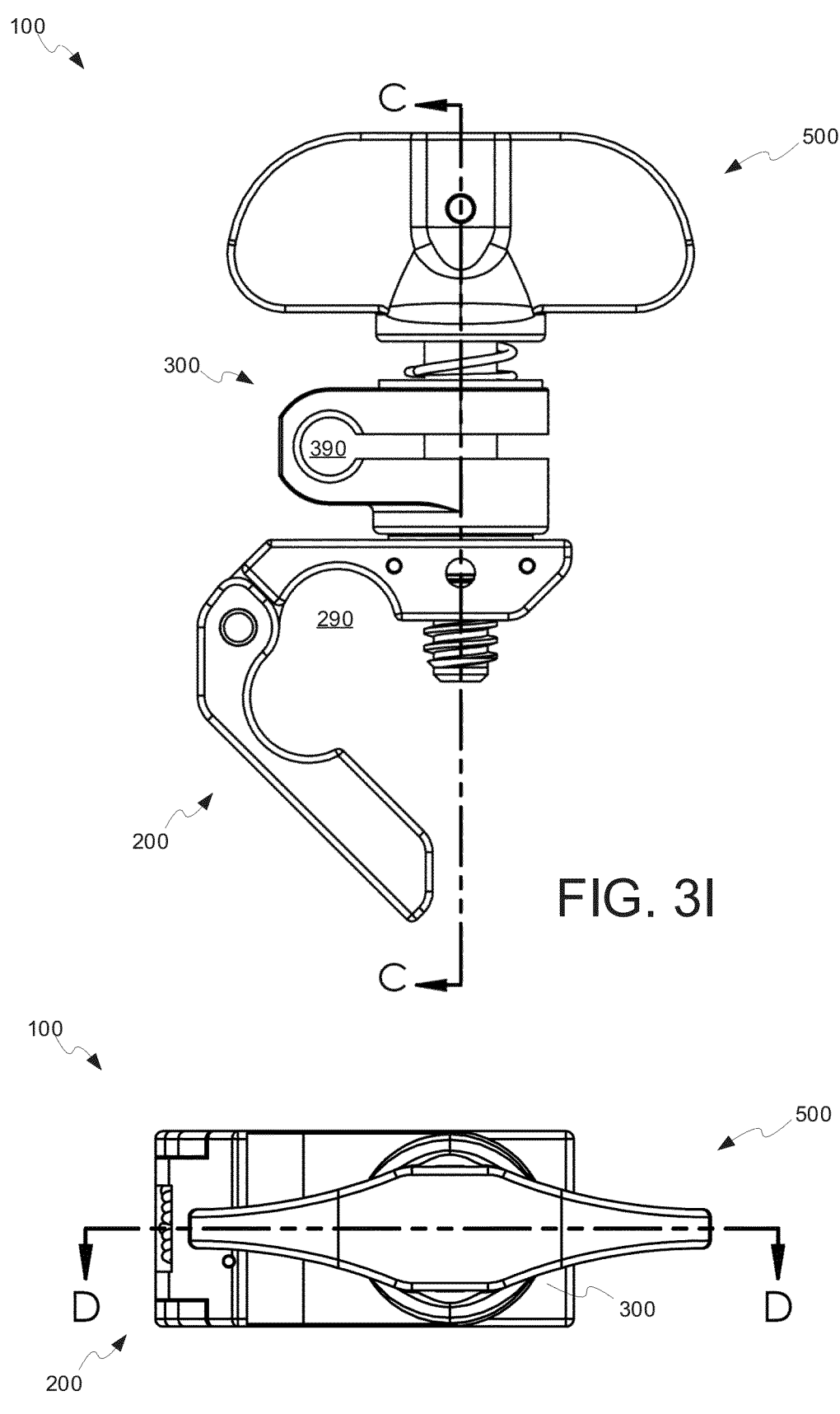
Figure 3K:
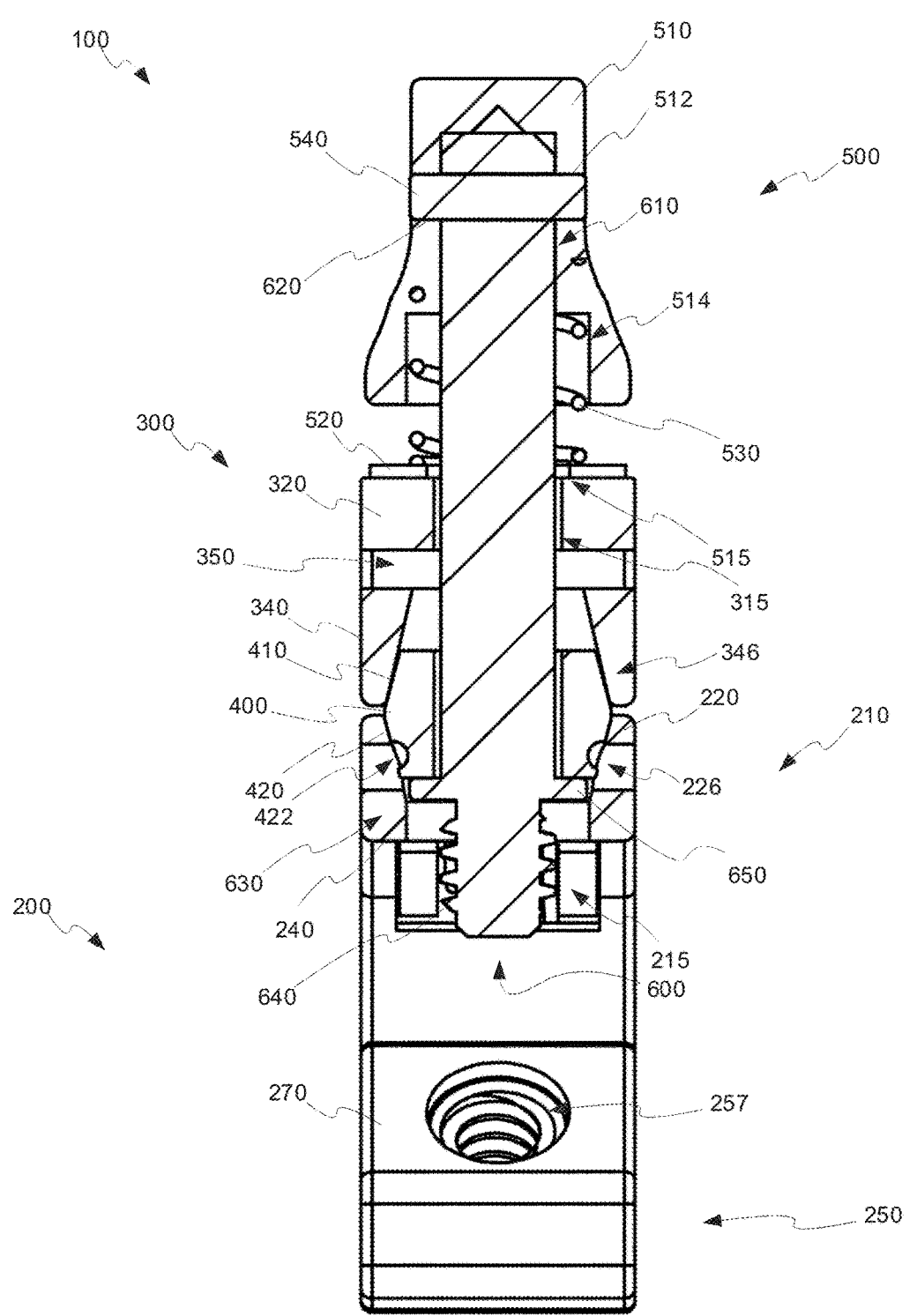
Figure 3L:
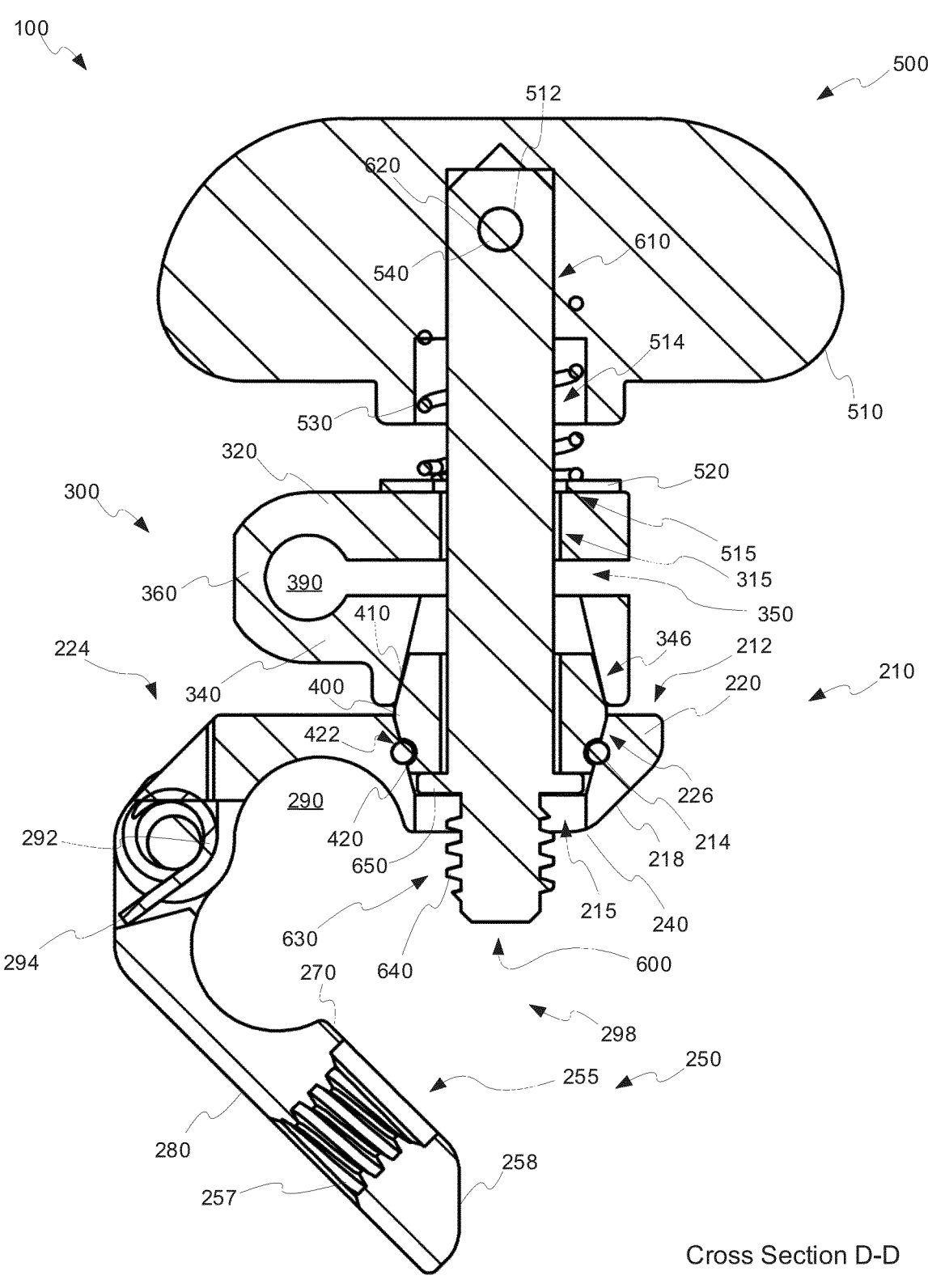
Figures 3M, 3N:
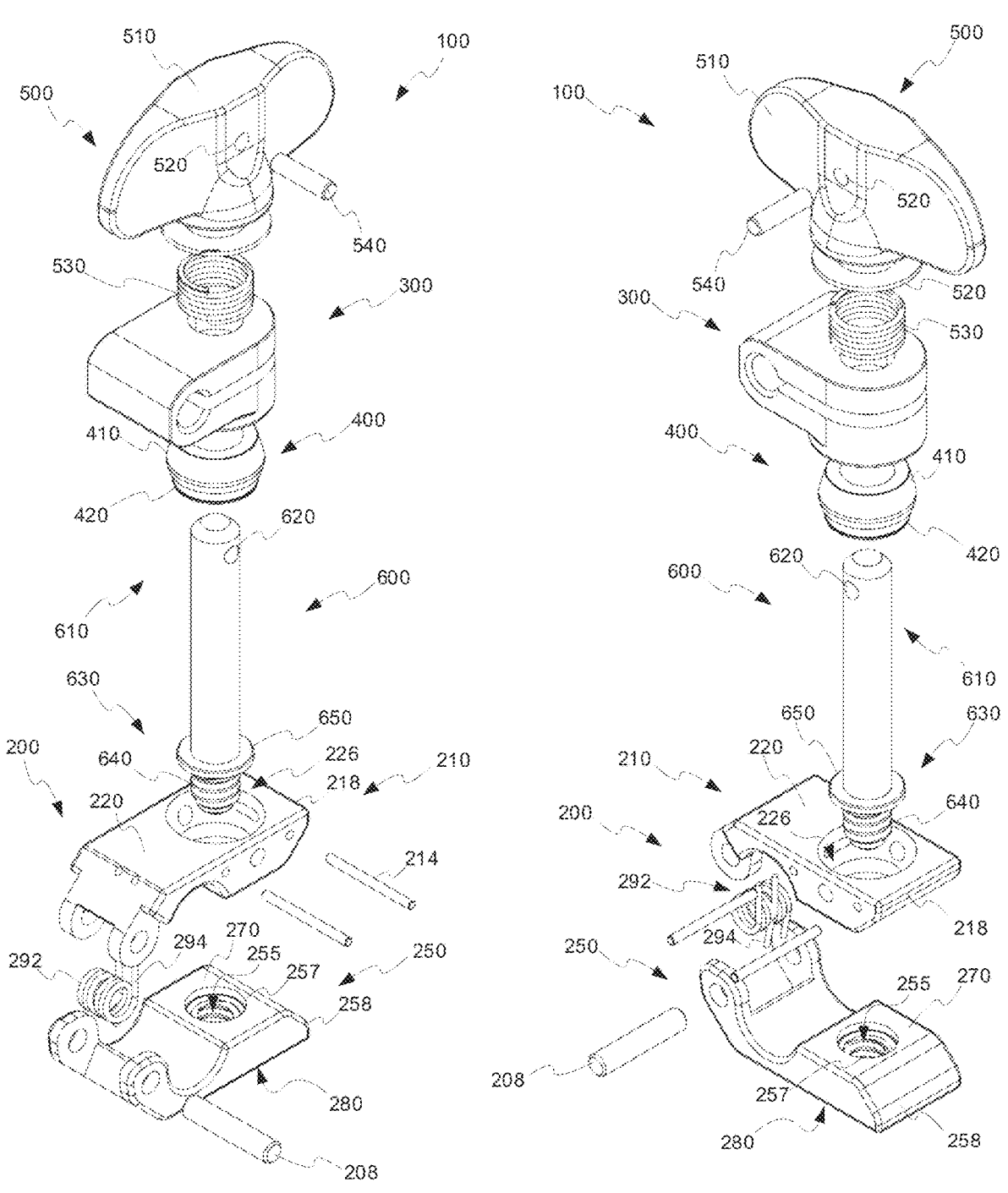
Figures 4A, 4B, 4C, 4D:
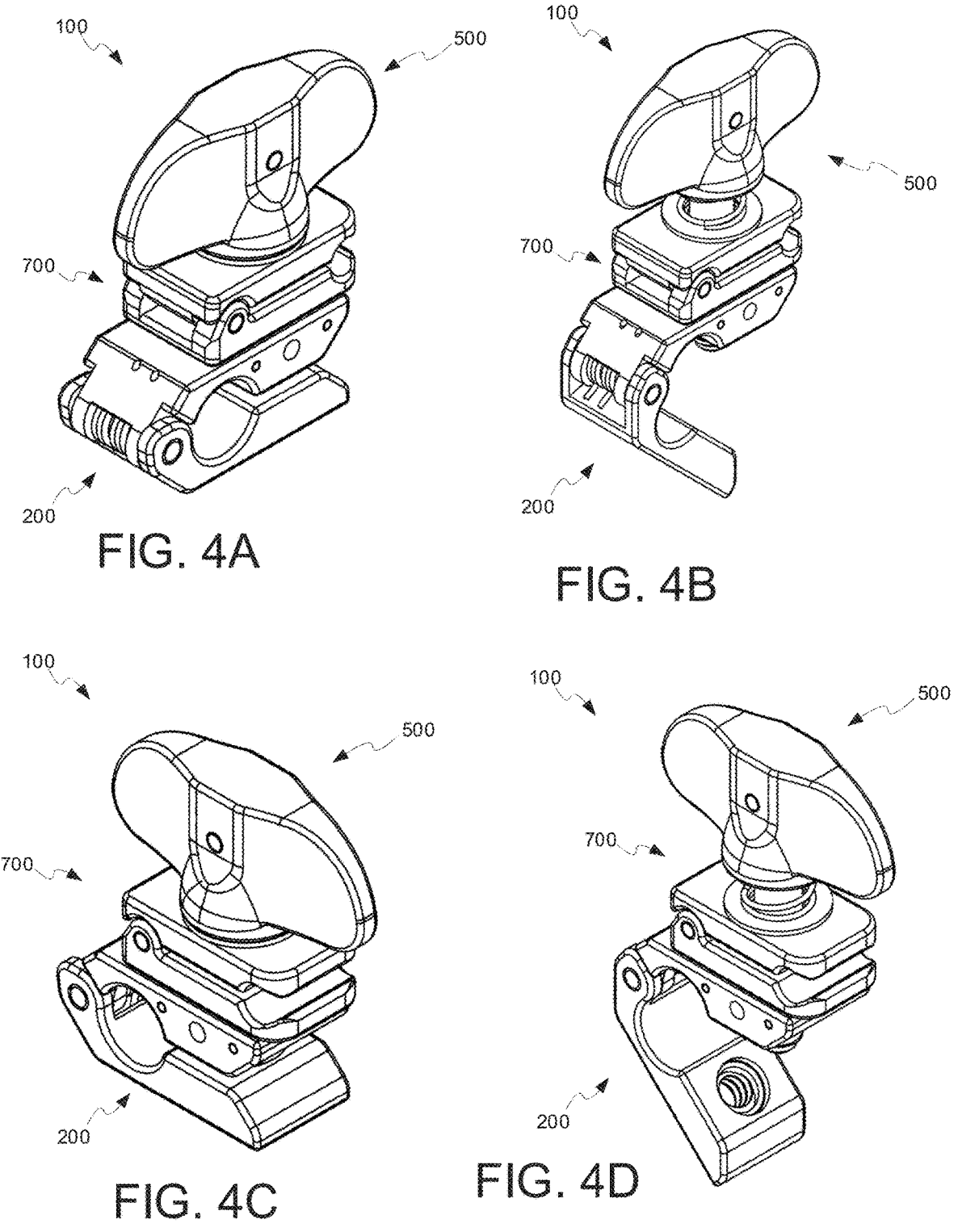
FIGS. 4A-4L provide various views of a second embodiment of a joint clamp for the retractor system shown in FIG. 1.
Figure 4E:
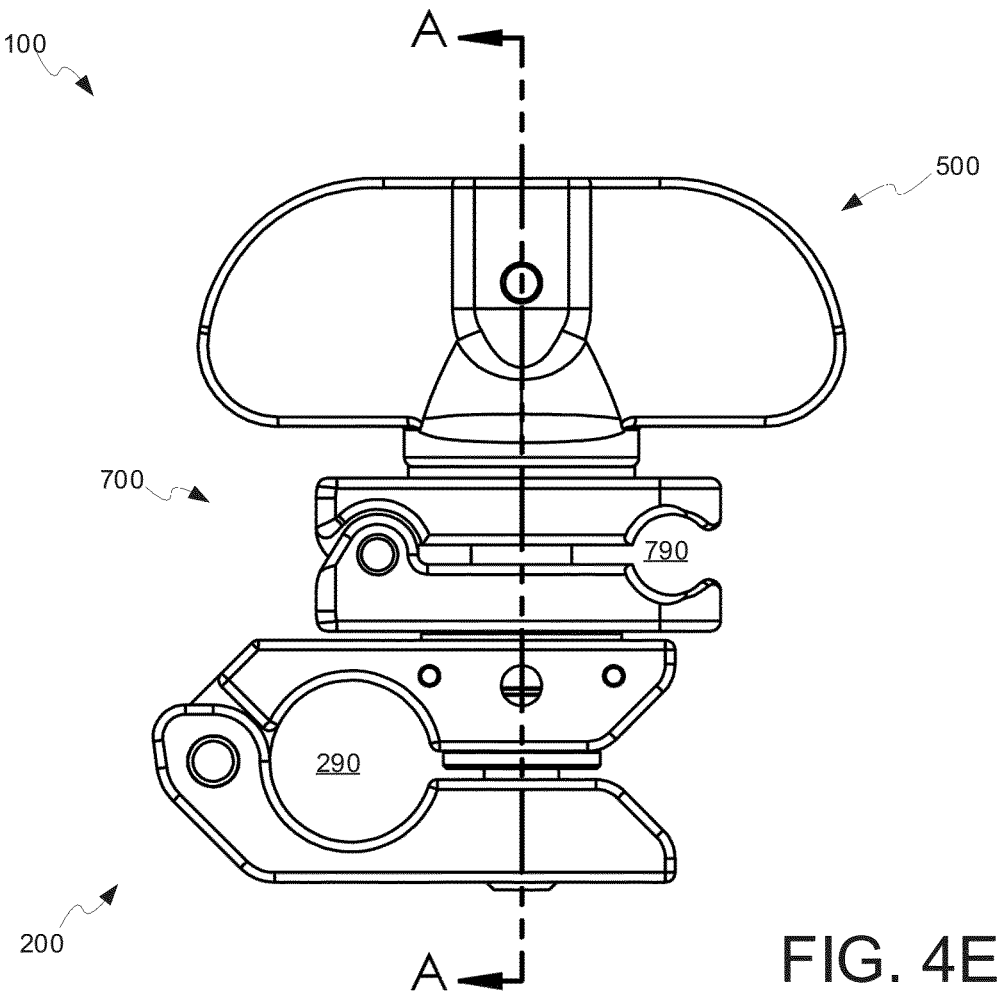
Figure 4F:
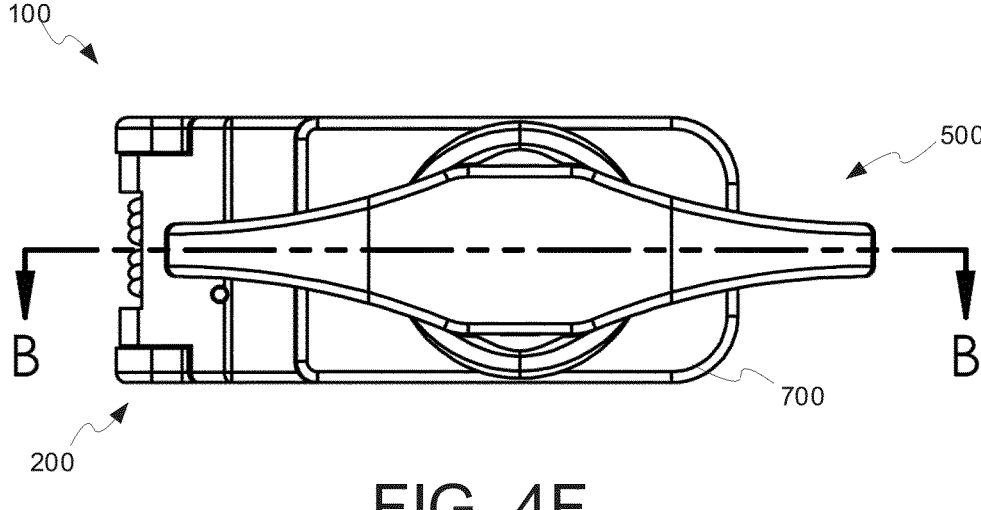
Figure 4G:
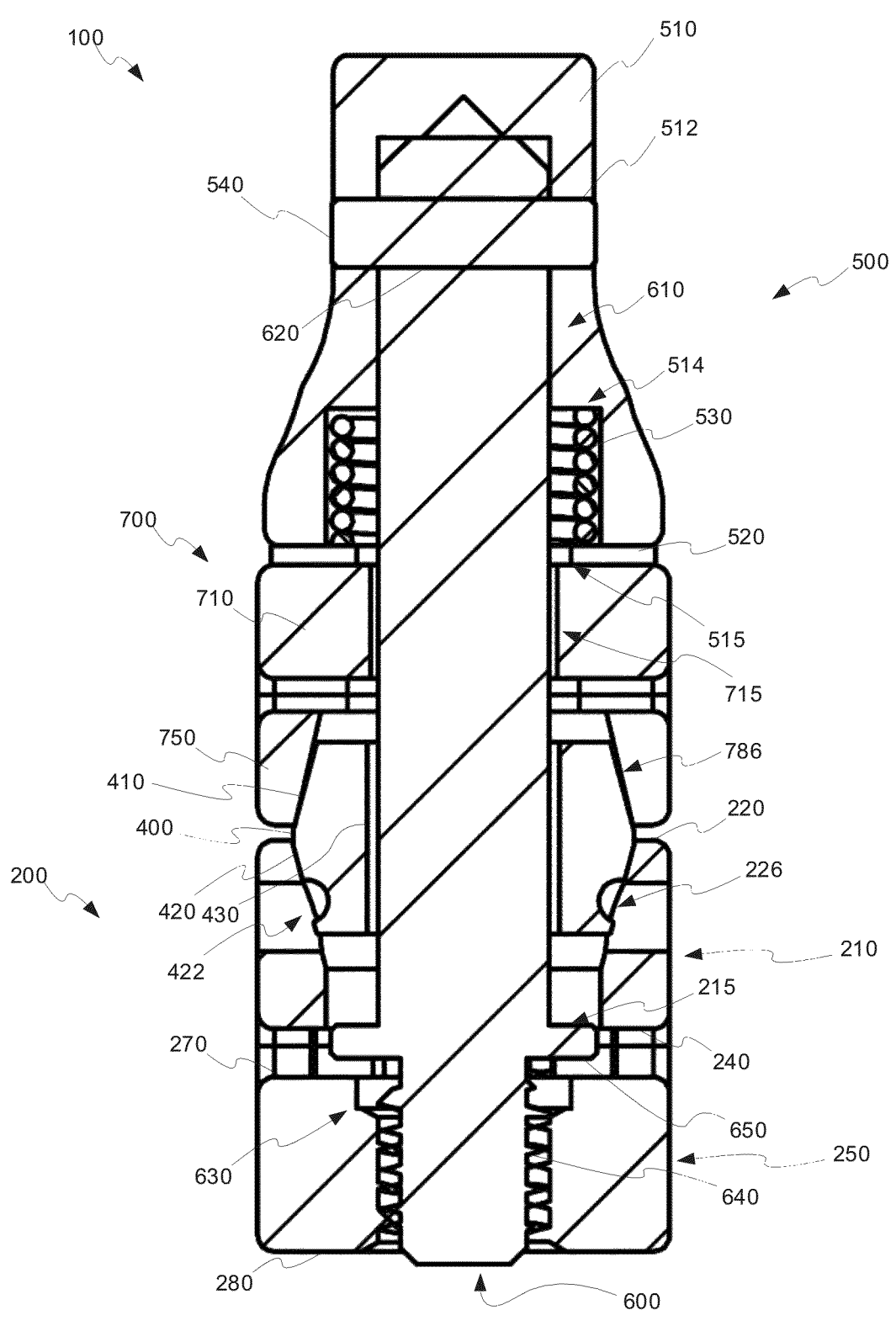
Figure 4H:
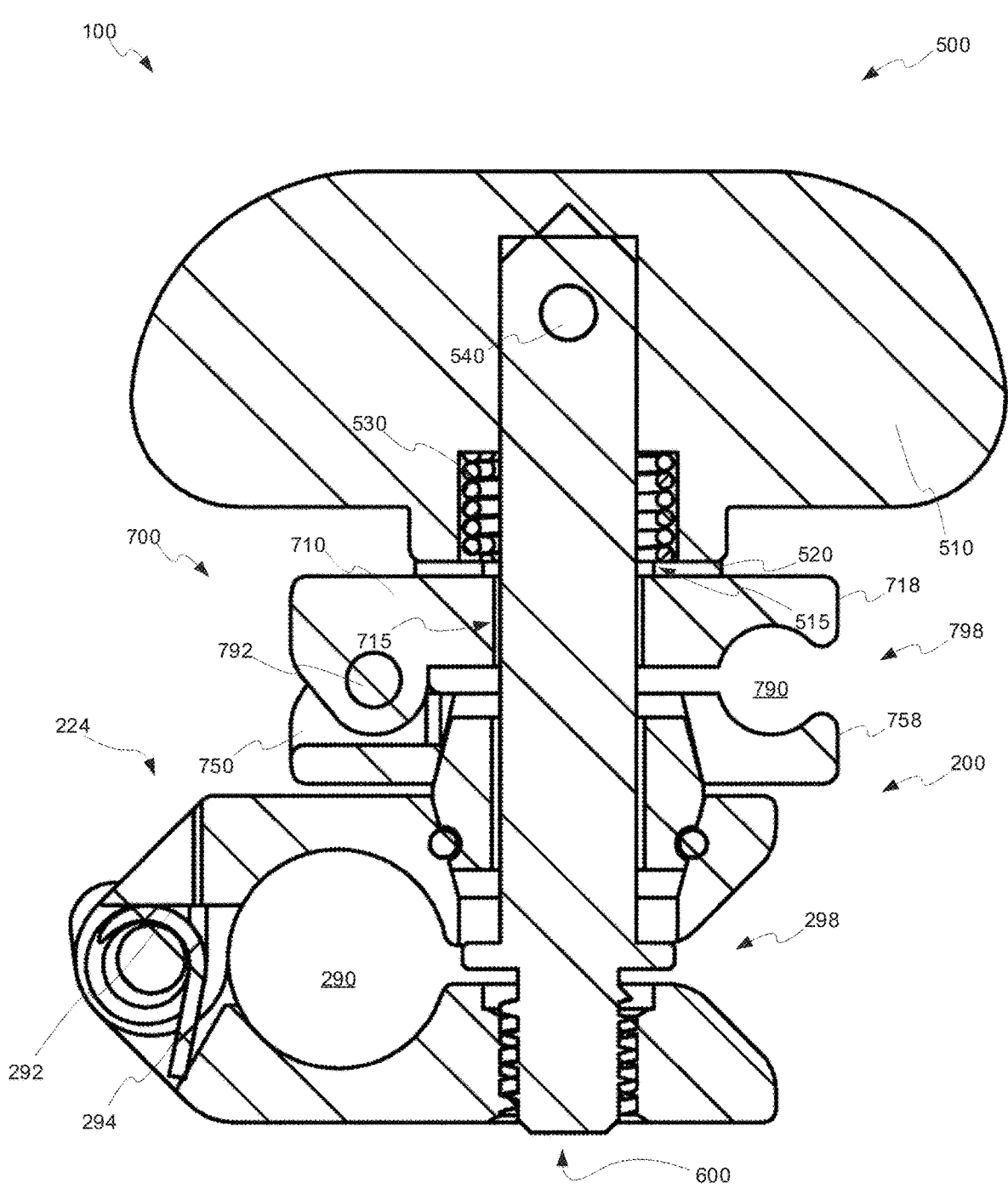
Figures 4I, 4J:
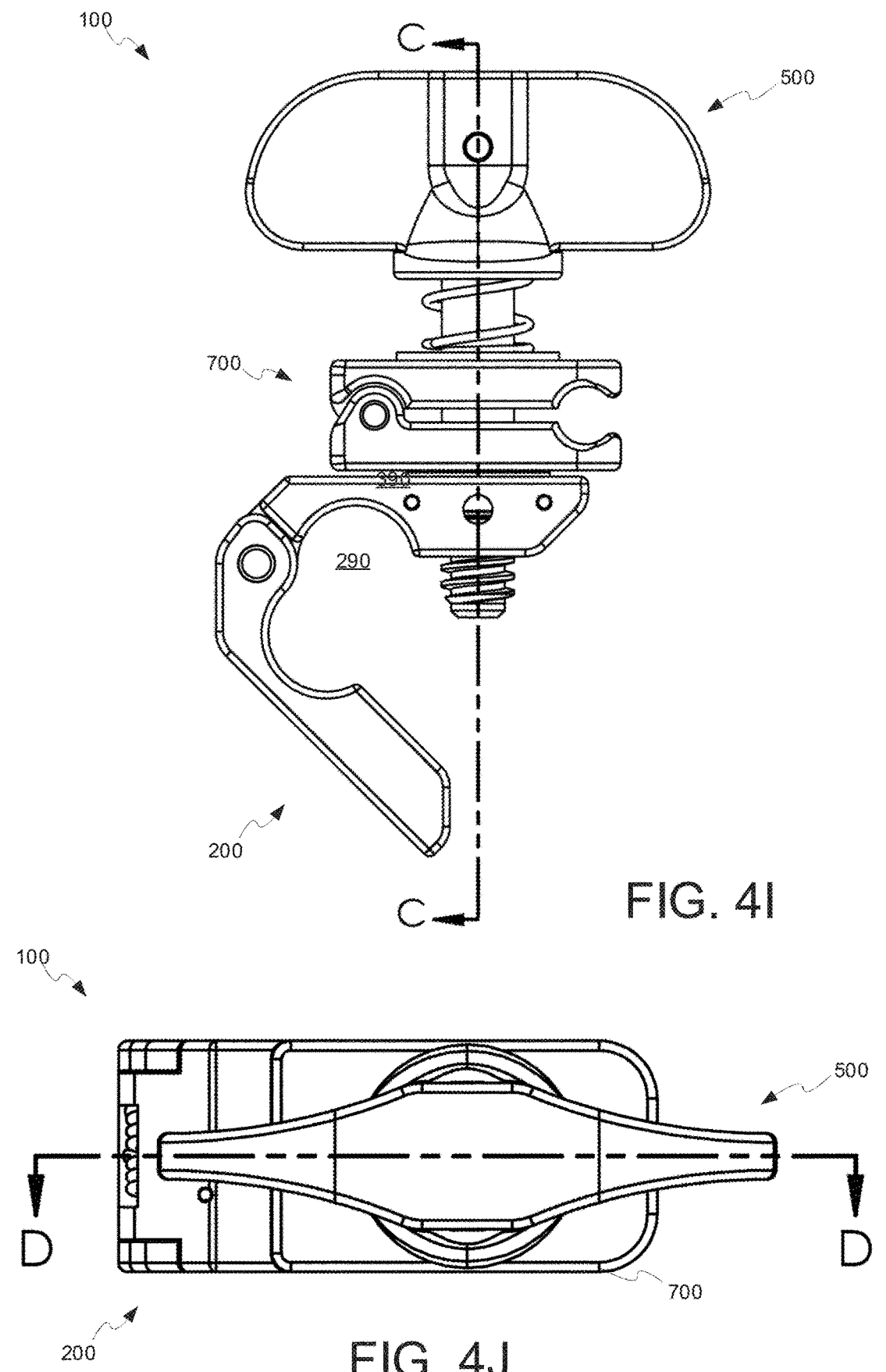
Figure 4K:
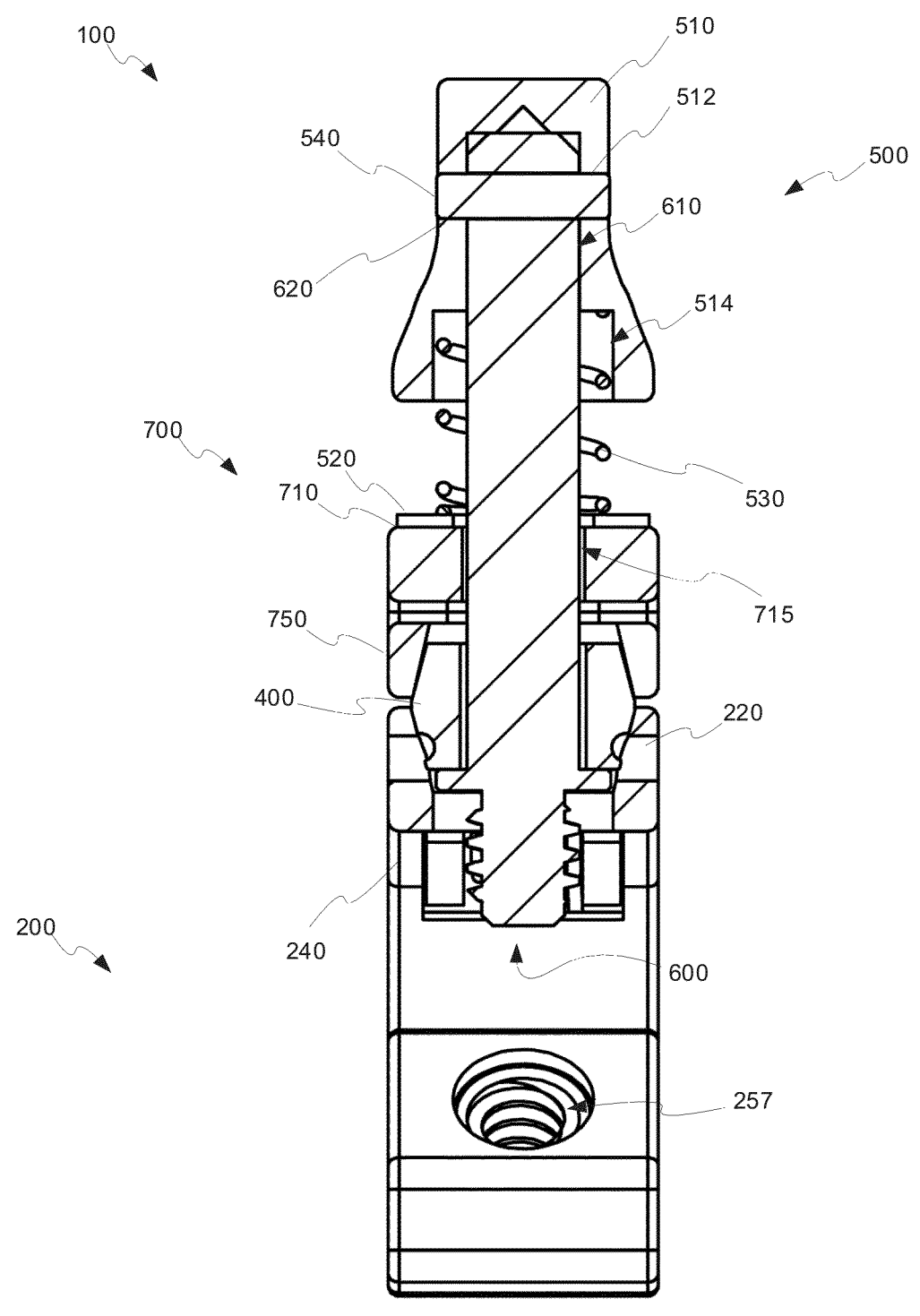
Figure 4L:
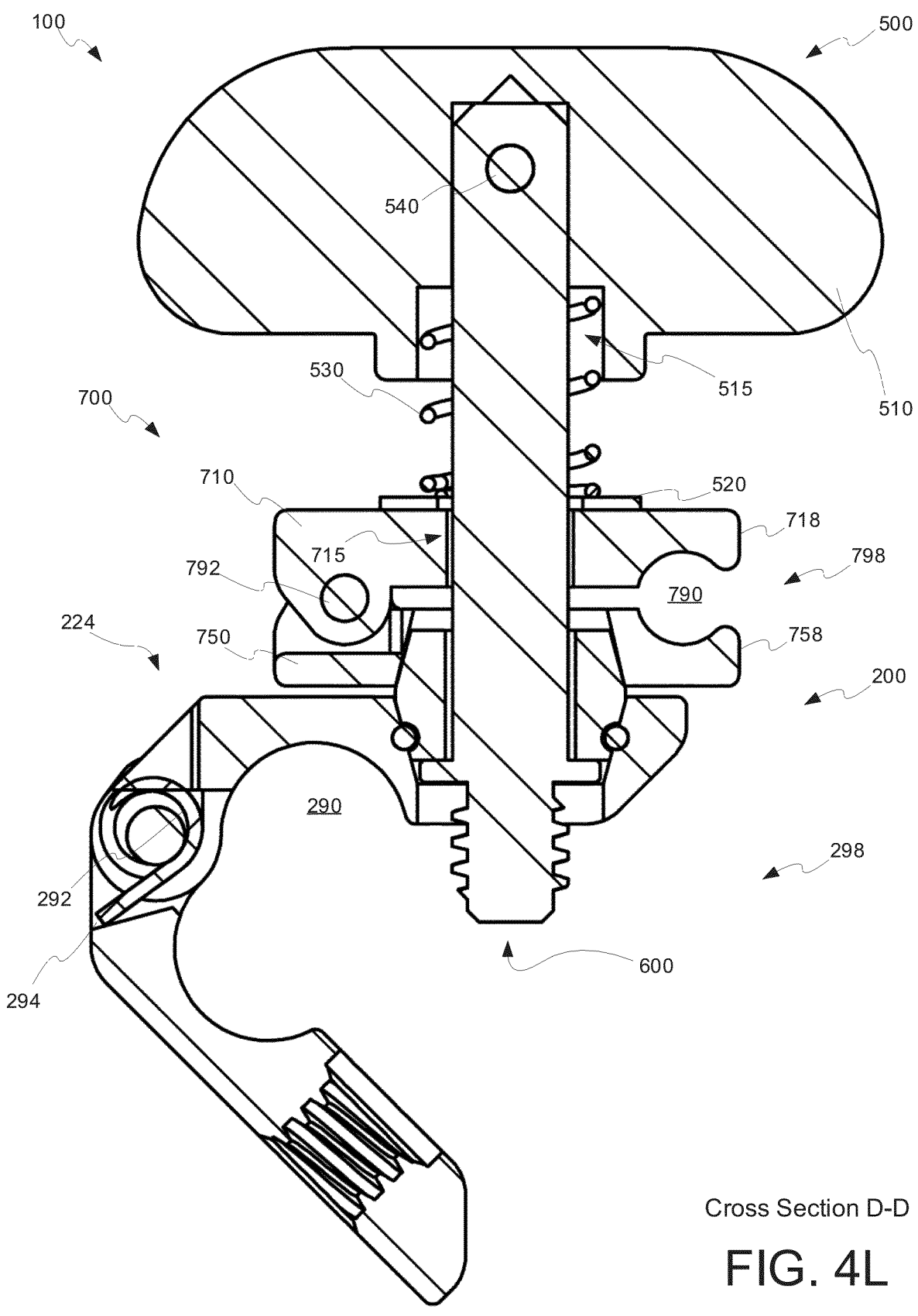

Referring to FIGS. 3A-3N, a first embodiment of a joint clamp 100 is shown. The joint clamp 100 may be suitable for one or more of the joint clamps 21, 22, 24, 26, 28 of FIGS. 1 and 2. The joint clamp 100 may include a snap clamp 200, a circle clamp 300, a bushing 400, a knob assembly 500, and a bolt 600. See, e.g., exploded views of FIGS. 3M-3N. While depicted with an upper circle clamp 300 and a lower snap clamp 200, the joint clamp 100 may be implemented with a different quantity and/or arrangement of clamps. For example, the joint clamp 100 may include three or more clamps of various assortments of circle clamps 300, snap clamps 200, and/or scissor clamps 700.

The bolt 600 may pass through bolt holes of the snap clamp 200, the circle clamp 300, and the bushing 400. An upper portion 610 of the bolt 600 may be coupled to a handle or knob 510 of the knob assembly 500. In particular, the knob 510 may include a hole 512 that passes through lateral sides of the knob 510. Similarly, the upper portion 610 of the bolt 600 may include a hole 620 that passes laterally through the bolt 600. A retaining pin 540 of the knob assembly 500 may pass through holes of the 520, 620 of the knob 510 and bolt 600 and secure the knob 510 to the upper portion 610 of the bolt 600.

A lower portion 630 of the bolt 600 may include one or more threads 640. The threads 640 may engage corresponding threads of the snap clamp 200 so as to secure the snap clamp 200 in a closed position. Moreover, the bolt 600 may include an annular flange 650 positioned above the threads 640. As explained in greater detail below, an upper surface of the annular flange 650 may engage the bushing 400 and prevent withdrawal of the bolt 600 from the snap clamp 200. In this manner, the bolt 600 retains the clamps 200, 300 in a stacked arrangement between the knob 510 and the annular flange 650.

The knob 510 may be rotated in a first direction (e.g., clockwise) that causes the threads 640 of the bolt 600 to engage threads 257 of the snap clamp 200 and draw the lower portion 250 toward the upper portion 210 of snap clamp 200. Conversely, the knob 510 may be rotated in a second direction (e.g., counter-clockwise) opposite the first direction that causes the threads 640 of the bolt 600 to force the lower portion 250 away from the upper portion 210 and eventually disengage the threads 257 of the snap clamp 200.

With particular reference to FIGS. 3G, 3H, and 3K-3N, details regarding the snap clamp 200 will be described. The snap clamp 200 may include an upper portion 210 and a lower portion 250. The upper portion 210 may include an upper surface 220 and a lower surface 240 with respective portions that are proximate the bolt 600 and respective portions that are distal from the bolt 600.

The upper portion 210 may include a bolt hole 215 that passes vertically through the upper portion 210. The upper surface 220 of the upper portion 210 may also include a bushing recess 226 in the proximal portion 212. The bushing recess 226 may include a frustoconical surface configured to engage a frustoconical bushing lower surface 420 of the bushing 400. In one embodiment, the bushing recess 226 and the bolt hole 215 are coaxially aligned with one another so as to permit the bolt 600 with its annular flange 650 to pass through the bushing recess 226 and the bolt hole 215. The bolt hole 215 and the bushing recess 226 may have a diameter greater than a diameter of the annular flange 650 of the bolt 600.

The lower portion 250 may include an upper surface 270 and a lower surface 280 with respective portions that are proximate the bolt 600 and distal portions that are distal from the bolt 600. The lower portion 250 may include a bolt hole 255 that passes vertically through the proximal portion 252 of the lower portion 250. The bolt hole 255 may include one or more threads 257. In one embodiment, the bolt hole 255 is coaxially aligned with the bushing recess 226 and the bolt hole 215 of the upper portion 210. Thus, the bolt 600 may pass through the bushing recess 226 and the bolt hole 215 of the upper portion 210 and into the bolt hole 255 of the lower portion 250 when the snap clamp 200 is in a closed position. Threads 640 of the bolt 600 may engage threads 257 of the lower portion 250 and either pull the bolt 600 into the bolt hole 255 or withdraw the bolt 600 from the bolt hole 255 based on a rotational direction of the bolt 600.

As shown, a pivot pin 208 may pivotally couple the upper portion 210 to the lower portion 250. In particular, the distal portion 224 of the upper portion 210 may include a pivot hole that passes through lateral sides of the distal portion 224. Similarly, the distal portion 254 of the lower portion 250 may include a pivot hole that passes through lateral sides of the distal portion 254. The pivot pin 208 may pass through the pivot holes and pivotally join the upper portion 210 to the lower portion 250. As a result, the upper portion 210 and the lower portion 250 may pivot about a longitudinal axis of the pivot pin 208.

As further shown, the pivot pin 208 may further pass through a spring 292 of the snap clamp 200 and help retain the spring 292 between the upper portion 210 and the lower portion 250. The spring 292 may include one or more helical torsion springs. As shown, the one or more helical torsion springs of spring 292 may include tabs 294 that engage surfaces of the upper portion 210 and the lower portion 250 and collectively exert a biasing force to the upper portion 210 and the lower portion 250. In particular, the biasing force may be sufficient to overcome gravitational forces and cause the lower portion 250 to pivot about the longitudinal axis of the pivot pin 208 to a closed position in which proximal portions 212, 252 of the upper and lower portions 210, 250 are placed in close proximity to one another and threads 640 of bolt 600 abut threads 257 of the lower portion 250. Due to such positioning, a person may merely turn the knob 510 to cause the threads 640 of the bolt 600 to engage the threads 257 of the lower portion 250 and draw the proximal portion 252 of the lower portion 250 toward the proximal portion 212 of the upper portion 210. In this manner, one may increase a clamping force applied by the snap clamp 200 upon an object passing through clamping passage 290.

The proximal portion 212 of the upper portion 210 may include an end 218 that is distal from the distal portion 224 of the upper portion 210. The end 218 may be tapered from the upper surface 211 to the lower surface 240. Similarly, the proximal portion 252 of the lower portion 250 may include an end 258 that is distal from the distal portion 254. The end 258 may be tapered from the lower surface 280 to the upper surface 270. The tapered surfaces of ends 218, 258 may define a mouth opening 298 via which an object may be received. The object may press against the tapered ends 218, 258, overcome the biasing force of the spring 292, and force the proximal portion 252 of the lower portion 250 away from the proximal portion 212 of the upper portion 210. In this manner, the object may pass through the mouth opening 298 and into the clamping passage 290.

The spring 292 of the snap clamp 200 may provide the snap clamp 200 with a snap-on feature. In particular, the spring 292 may provide a biasing force greater than a force applied by gravity to the lower portion 250. Thus, the biasing force of the spring 292 may overcome the gravitation force on the lower portion 250 and may bias the mouth opening 298 toward a closed or receiving position. See, e.g., FIG. 3A.

While the mouth opening 298 is in the receiving position, an object such as a frame member, a retractor handle, etc. may be pressed against the mouth opening 298 with sufficient force to overcome the biasing force of the spring 292 so as to expand the mouth opening 298 and permit the object to pass between the proximal portions 212, 252 and into a clamping passage 290 defined by the upper portion 210 and the lower portion 250. Once passed the proximal portions 212, 252 and into the clamping passage 290, the spring 292 may bias the proximal portion 212, 252 back toward the closed or receiving position so as to retain the object in the clamping passage 290. Conversely, the object may be pulled from clamping passage 290 of the snap clamp 200 with sufficient force to overcome the biasing force of the spring 292 so as to expand the mouth opening 298 and permit the object to pass between the proximal portions 212, 252 and out of the clamping passage 290. Again, once passed the proximal portions 212, 252, the spring 292 may bias the proximal portions 212, 252 back toward the closed position.

In this manner, the snap clamp 200 may be snapped-on an object by pushing the snap clamp 200 against the object with a snap-on force that overcomes the biasing force of the spring 292, and the snap clamp 200 may be removed from the object by pulling the snap clamp 200 away from the object with a snap-off force that overcomes the biasing force of the spring 292. In certain embodiments, the biasing force of the spring 292 sufficiently biases the proximal portions of the upper and lower portions 210, 250 toward the closed direction so as to require the snap-off force to be greater than a gravitational force exerted by the snap clamp 200. In this manner, the spring 292 and associated snap-off force prevent the snap clamp 200 from detaching from the object due to its own weight once snapped onto the object even when the threads 640 of the bolt 600 are not engaged with the threads 257 of the lower portion 250. Furthermore, the biasing force provided by spring 292 may be sufficiently large so as to cause an audible snapping sound as the object moves into the clamping passage 290 and the lower portion 250 snaps upward toward the upper portion 210.

For example, when threads 640 of the bolt 600 do not engage threads 257 of the joint clamp 100, the snap clamp 200 may be snapped-on a frame member via application of a snap-on force that causes the frame member to pass through the mouth opening 298, passed proximal portions of the upper and lower portions 210, 250, and into the clamping passage 290. Similarly, when threads 640 of the bolt 600 do not engage threads 257 of the snap clamp 200, the snap clamp 200 may be snapped-off or removed from the frame member via application of a snap-off force that causes the object to move from the clamping passage 290, passed proximal portions of the upper and lower portions 210, 250, and out the mouth opening 298.

From the above, it should be appreciated that a person may attach and secure the snap clamp 200 to an object such as a frame member without manually closing the snap clamp 200. The biasing force is sufficient to close the snap clamp 200 and abut the threads 257, 640. As such, the person may snap the snap clamp 200 onto an object and turn the knob 510 to engage threads 640 of the bolt 600 with the threads 257 of the lower portion 250 and apply a clamping force to the object in the clamping passage 290. Such operation may free a hand of the person, that would otherwise be used to close the snap clamp 200, for other tasks such as positioning or limiting movement of a retractor blade attached to the joint clamp 100 while securing the joint clamp 100 to a frame member via the snap clamp 200.

Continuing to refer to FIGS. 3A-3N, details of the circle clamp 300 are described. In particular, the circle clamp 300 may include an upper portion 320 and a lower portion 340 connected at a fulcrum 360. A bolt hole 315 may extend vertically through the upper and lower portions 320, 340. The bolt hole 315 may have a diameter greater than a diameter of the bolt 600 to permit passage of the bolt 600 through the upper and lower portions 320, 340.

The lower portion 340 may include a frustoconical bushing recess 346 in a lower surface of the lower portion 340. The bushing recess 346 may be configured to receive a frustoconical bushing upper surface 410 of the bushing 400. Furthermore, the bolt hole 315 may extend vertically through the bushing recess 346. Moreover, a longitudinal axis of the bolt hole 315 may be coaxially-aligned with a longitudinal axis of the bushing recess 346.

The circle clamp 300 may further include a circular clamping passage 390. The circular clamping passage 390 may pass through lateral sides of the upper portion 320 and lateral sides of the lower portion 340 at a location proximal the fulcrum 360. A longitudinal axis of the clamping passage 390 may be perpendicular to the longitudinal axes of the bolt hole 315 through the circle clamp 300. However, in other embodiments, the circle clamp 300 may orient the longitudinal axis of the clamping passage 390 differently with regard to the longitudinal axes of the bolt hole 315 through the circle clamp 300.

The clamping passage 390 may permit an object such as a frame member, a retractor handle, etc. to pass laterally through the circle clamp 300. For example, the clamping passage 390 may be sized to accommodate the cross bar 18 of FIG. 2. As shown, the circle clamp 300 may include a gap 350 between the lower surface of the upper portion 320 and the upper surface of the lower portion 340. The gap 350 may permit a clamping force to squeeze the circle clamp 300 and tighten a grip on the object passing through the clamping passage 390. In particular, the clamping force may move the upper portion 320 and the lower portion 340 toward one another, thus reducing a circumference or diameter of the clamping passage 390 and constricting the area within clamping passage 390.

As shown in FIGS. 3G, 3H, and 3K-3N, the joint clamp 100 may include the bushing 400 between the snap clamp 200 and the circle clamp 300. In particular, the bushing 400 may include a frustoconical bushing upper surface 410, a frustoconical bushing lower surface 420, and a bolt hole 430. The bushing upper surface 410 may be configured to engage the bushing recess 346 in the lower portion 340 of the circle clamp 300. Similarly, the bushing lower surface 420 may be configured to engage a bushing recess 226 of the snap clamp 200. The bolt hole 430 may pass vertically through the bushing 400 and may have a diameter greater than a diameter of the upper portion 610 of the bolt 600 to permit passage of upper portion 610 of the bolt 600 through the bushing 400. Moreover, the diameter of the bolt hole 430 may be smaller than a diameter of the annular flange 650 of the bolt 600 to prevent passage of the lower portion 630 of the bolt 600 through the bushing 400. A longitudinal axis of the bushing 400 may be coaxial with the longitudinal axis of the bolt 600 and the longitudinal axis of the bolt hole 430.

As best shown in FIGS. 3H, 3M, and 3N, the bushing lower surface 420 may further include an annular groove 422. The annular groove 422 engages retaining rods 214 that pass through lateral sides of the upper portion 210 of the snap clamp 200. The retaining rods 214 may permit the bushing 400 to rotate with respect to the snap clamp 200 about the longitudinal axis of the bushing 400, but prevent withdrawal of the bushing 400 from the bushing recess 226 in the upper portion 210 of the snap clamp 200. Thus, when assembled, the retaining rods 214 may prevent withdrawal of the bushing 400 from the snap clamp 200 and the bushing 400 may prevent annular flange 650 of the bolt 600 passed the bushing 400. In this manner, the circle clamp 300 and the snap clamp 200 may be maintained in a stacked arrangement between the knob 510 and the annular flange 650 of the bolt 600.

As shown in FIGS. 3M-3N, the knob assembly 500 may include the knob 510, a washer 520, a spring 530, and a retaining pin 540. The knob 510 may include a hole 512 through lateral sides of the knob 510. The retaining pin 540 may pass through the hole 512 of the knob 510 and through the hole 620 of the bolt 600. In this manner, the knob 510 may be coupled to the upper portion 610 of the bolt 600 in a manner that translates rotation of the knob 510 about a longitudinal axis of the bolt 600 into rotation of the bolt 600 about the longitudinal axis of the bolt 600.

As shown in the cross-sectional views of FIGS. 3G, 3H, 3K, and 3L, the bolt 600 may pass through the spring 530. Moreover, the spring 530 may be positioned between the knob 510 and the washer 520. A lower surface of the knob 510 may have a recess 514 configured to receive the spring 530. Moreover, a depth of the recess 514 in one embodiment is sufficient to completely receive the spring 530 when the snap clamp 200 is in a closed position. See, e.g., FIGS. 3G and 3H.

The washer 520 may have a generally cylindrical-shape with planar upper and lower surfaces. The lower surface of the washer 520 may engage an upper surface of the circle clamp 300. The upper surface of the washer 520 may engage a lower portion of the spring 530 and help prevent wear of the circle clamp 300 from rotational friction that the spring 530 would otherwise exert on the circle clamp 300. As shown, the washer 520 may further include a bolt hole 515 that extends through the upper and lower surfaces. The bolt hole 515 may have a diameter greater than a diameter of the bolt 600 so as to permit passage of the bolt 600 through the washer 520.

The spring 530 may bias the knob 510 upwardly away from the snap clamp 200. As shown in FIGS. 3K and 3L, such biasing force of the spring 530 may displace the knob 510 upward and partially retract the lower portion 630 of the bolt 600 into the bolt hole 215 of the snap clamp 200. Such retraction of the lower portion 630 may aid in snapping the snap clamp 200 onto and/or from an object as a smaller portion of the bolt 600 protrudes from the lower surface 240 than if the lower portion 630 were not retracted in to bolt hole 215.

When the snap clamp 200 is in the open position, the clamps 200, 300 are loosely coupled to the knob 510 via the bolt 600 and may be rotated relative to one another about a longitudinal axis of the bolt 600. The annular flange 650 of the bolt 600 may prevent clamps 200, 300 from being slid off the portion 630 of the bolt 600. The removed or reduced compression on clamps 200, 300 may cause clamping passage 290, 390 to expand their diameter, allowing clamps 200, 300 to be moved relative to objects such as frame members, retractor handles, etc. passing through the cylindrical clamping passages 290, 390.

Furthermore, when the snap clamp 200 is in the open position, the snap clamp 200 and the circle clamp 300 are able to rotate with respect to each other about the longitudinal axis of the bolt 600. Such rotation provides greater freedom to position attached objects such as frame members, retractor handles, etc. in a desired manner. The ability to rotate the clamps 200, 300 may be locked or unlocked by the knob 510. When the knob 510 places the snap clamp 200 in the open position, the snap clamp 200 and the circle clamp 300 may rotate with respect to each other about a longitudinal axis of the bolt 600. When the knob 510 places the snap clamp 200 in the closed position, rotation of the snap clamp 200 with respect to the circle clamp 300 is made extremely difficult, with the result establishing a fixed position for the clamps 200, 300 with respect to each other so long as the knob 510 maintains the snap clamp 200 in the locked position. As the knob 510 is rotated and the snap clamp 200 is place into the closed position, the upper portion 210 of the snap clamp 200 is pressed against the bushing 400 with greater force, and the lower portion 340 of the circle clamp 300 is also pressed against the bushing 400 with greater force. This greater force creates greater friction between the snap clamp 200 and the bushing 400 and between the circle clamp 300 and the bushing 400, greatly restricting the ability of the snap clamp 200 and the circle clamp 300 to rotate with respect to each other.

Referring now to FIGS. 4A-4H, a second embodiment of a joint clamp is shown. The joint clamp 101 of FIGS. 4A-4H and the joint clamp 100 shown in FIGS. 3A-3N are implemented in a similar manner. However, the joint clamp 101 differs from the joint clamp 100 in that the circle clamp 300 of the joint clamp 100 is replaced with a two-piece clamp 700. As such, similar components of the joint clamp 101 are presented with the same references numerals as corresponding elements of the joint clamp 100 and generally not further described below. Instead, the following generally focuses on the two-piece clamp 700 with particular reference to FIGS. 4G, 4H, 4K, and 4L.

The two-piece clamp 700 may include an upper portion 710 and a lower portion 750. The upper portion 710 may include an upper surface and a lower surface with respective proximal portions that are proximate the bolt 600, respective first distal portions that are distal from the bolt 600, and respective second distal portions that are distal from the bolt 600 and opposite the respective first distal portions.

The upper portion 710 may include a bolt hole 715 that passes vertically through the upper portion 710. The bolt hole 715 may have a diameter greater than a diameter of the upper portion 610 of the bolt 600.

The lower portion 750 may include an upper surface and a lower surface with respective portions that are proximate the bolt 600 and portions that are distal from the bolt 600. The lower surface of the lower portion 750 may include a bushing recess 786 in its proximal portion. The bushing recess 786 may include a frustoconical surface configured to engage the frustoconical bushing upper surface 410 of the bushing 400. In one embodiment, the bushing recess 786 and the bolt hole 715 are coaxially aligned with one another so as to permit the upper portion 610 of the bolt 600 to pass through the bushing recess 786 and the bolt hole 715.

As shown, a pivot pin 792 may pivotally couple the upper portion 710 to the lower portion 750. In particular, the first distal portion of the upper portion 710 may include a pivot hole that passes through lateral sides of its first distal portion. Similarly, the first distal portion of the lower portion 250 may include a pivot hole that passes through lateral sides of its first distal portion. The pivot pin 792 may pass through the pivot holes and pivotally join the upper portion 710 to the lower portion 750. As a result, the upper portion 710 and the lower portion 750 may pivot about a longitudinal axis of the pivot pin 792.

The second distal portion of the upper portion 710 may include an end 718 that is distal from the first distal portion of the upper portion 710. Similarly, the second distal portion of the lower portion 750 may include an end 758 that is distal from the first distal portion of the upper portion 710. The ends 718, 758 may define a mouth opening 798 via which an object may be received. The object may press against the ends 718, 758, overcome the biasing force of the spring 530 of the knob assembly 500, and force the end 758 of the lower portion 750 away from the end 718 of the upper portion 710. In this manner, the object may pass through the mouth opening 798 and into a clamping passage 796 defined by the second distal portions of the upper and lower portions 710, 750.

The spring 530 of the knob assembly 500 may provide the two-piece clamp 700 with a clip-on feature. In particular, the spring 530 may provide a biasing force greater than a force applied by gravity to the lower portion 750. Thus, the biasing force of the spring 530 may overcome the gravitation force on the lower portion 750 and may bias the mouth opening 798 toward a closed or receiving position. See, e.g., FIG. 4A.

While the mouth opening 798 is in the receiving position, an object such as a frame member, a retractor handle, etc. may be pressed against the mouth opening 798 with sufficient force to overcome the biasing force of the spring 530 so as to expand the mouth opening 798 and permit the object to pass between the proximal portions of the upper and lower portions 710, 750 and into a clamping passage 796 defined by the second distal portions of the upper and lower portions 710, 750. Once passed the ends 718, 758 and into the clamping passage 796, the spring 530 may bias the ends 718, 758 back toward the closed or receiving position so as to retain the object in the clamping passage 796. Conversely, the object may be pulled from clamping passage 796 with sufficient force to overcome the biasing force of the spring 530 so as to expand the mouth opening 798 and permit the object to pass between the ends 718, 758 and out of the clamping passage 796. Again, once passed the ends 718, 758, the spring 530 may bias the ends 718, 758 back toward the closed position.

In this manner, the two-piece clamp 700 may be snapped-on an object by pushing the two-piece clamp 700 against the object with a clip-on force that overcomes the biasing force of the spring 530, and the two-piece clamp 700 may be removed from the object by pulling the two-piece clamp 700 away from the object with a snap-off force that overcomes the biasing force of the spring 530. In certain embodiments, the biasing force of the spring 530 sufficiently biases the upper and lower portions 710, 750 toward the closed direction so as to require the snap-off force to be greater than a gravitational force exerted by the two-piece clamp 700. In this manner, the spring 530 and associated snap-off force prevent the two-piece clamp 700 from detaching from the object due to its own weight once snapped onto the object even when the threads 640 of the bolt 600 are not engaged with the threads 257 of the lower portion 250 of the snap clamp 200. Furthermore, the biasing force provided by spring 530 may be sufficiently large so as to cause an audible snapping sound as the object moves into the clamping passage 790 and the lower portion 750 snaps upward toward the upper portion 710.

While particular embodiments of the invention have been shown, the invention is not limited thereto since modifications may be made by those skilled in the art, particularly in light of the foregoing teaching. It is, therefore, the appended claims which define the true spirit and scope of the invention.

What is claimed is:

1. A joint clamp for a surgical retractor system, the joint clamp comprising:
   a clamp upper portion;
   a clamp lower portion pivotally coupled to the clamp upper portion, wherein the clamp lower portion comprises a threaded bore into an upper surface of the clamp lower portion;
   a clamping passage that passes laterally between the clamp upper portion and the clamp lower portion;
   a bolt that pass vertically through the clamp upper portion, wherein the bolt comprises a bolt upper portion and a bolt lower portion, and wherein the bolt lower portion comprises threads;
   a knob coupled to the bolt upper portion; and
   a spring that exerts a biasing force on the clamp lower portion;
   wherein the biasing force urges the clamp lower portion to pivot toward the clamp upper portion and abut the threaded bore of the clamp lower portion against the threads of the bolt lower portion; and
   wherein rotation of the knob in a first direction rotates the bolt such that the threads of the bolt lower portion engage the threaded bore of the clamp lower portion and draw the clamp lower portion toward the knob.

2. The joint clamp of claim 1, wherein rotation of the knob in the first direction increases a clamping force exerted by the clamp upper portion and the clamp lower portion upon an object in the clamping passage.

3. The joint clamp of claim 1, wherein the spring comprises one or more torsion springs that engage the clamp upper portion and the clamp lower portion and collectively exert the biasing force upon the clamp lower portion.

4. The joint clamp of claim 3, comprising a pivot pin that laterally passes through the clamp upper portion and the clamp lower portion and through the one or more torsion springs.

5. The joint clamp of claim 4, wherein the clamping passage is positioned between the pivot pin and the bolt lower portion.

6. The joint clamp of claim 4, wherein ends of the clamp upper portion and the clamp lower portion that are distal from the pivot pin are tapered to laterally guide an object into the clamping passage.

7. The joint clamp of claim 1, wherein the biasing force exerted by the spring is sufficient to overcome a gravitational force exerted on the clamp lower portion and abut the threaded bore of the clamp lower portion against the threads of the bolt lower portion.

8. The joint clamp of claim 1, comprising:

an upper spring between the knob and the clamp upper portion; and wherein the upper spring biases the knob away from the clamp upper portion.

9. The joint clamp of claim 8, wherein:

the clamp upper portion comprises a bolt hole; and the upper spring, via its biasing of the knob, partially retracts the bolt lower portion into the bolt hole.

10. The joint clamp of claim 1, wherein the spring causes the lower clamp portion to generate an audible sound in response to snapping toward the clamp upper portion.

11. A joint clamp for a surgical retractor system, the joint clamp comprising:

a handle;

a clamp upper portion;

a clamp lower portion pivotally coupled to the clamp upper portion, wherein the clamp lower portion comprises threads;

a clamping passage that passes between the clamp upper portion and the clamp lower portion;

a bolt that passes through the clamp upper portion, wherein the bolt comprises a bolt upper portion coupled to the handle and a bolt lower portion comprising threads; and a spring that exerts a biasing force on the clamp lower portion and pivots the threads of the lower clamp portion toward the threads of the bolt lower portion; and wherein rotation of the handle in a first direction rotates the bolt and causes the threads of the bolt lower portion to engage the threads the clamp lower portion, draw the clamp lower portion toward the clamp upper portion, and reduce the clamping passage between the clamp upper portion and the clamp lower portion.

12. The joint clamp of claim 11, wherein rotation of the handle in the first direction increases a clamping force exerted upon an object in the clamping passage.

13. The joint clamp of claim 11, wherein the spring comprises one or more torsion springs that engage the clamp upper portion and the clamp lower portion and collectively exert the biasing force upon the clamp lower portion.

14. The joint clamp of claim 13, comprising a pivot pin that laterally passes through the clamp upper portion and the clamp lower portion.

15. The joint clamp of claim 14, wherein the clamping passage is positioned between the pivot pin and the bolt lower portion.

16. The joint clamp of claim 14, wherein ends of the clamp upper portion and the clamp lower portion that are distal from the pivot pin are tapered to laterally guide an object into the clamping passage.

17. The joint clamp of claim 11, wherein the biasing force exerted by the spring is sufficient to overcome a gravitational force exerted on the clamp lower portion and abut the threads of the clamp lower portion against the threads of the bolt lower portion.

18. The joint clamp of claim 11, comprising:

an upper spring between the handle and the clamp upper portion; and wherein the upper spring biases the handle away from the clamp upper portion.

19. The joint clamp of claim 18, wherein:

the clamp upper portion comprises a bolt hole; and the upper spring, via its biasing of the handle, partially retracts the bolt lower portion into the bolt hole.

20. The joint clamp of claim 11, wherein the spring causes the lower clamp portion to generate an audible sound in response to snapping toward the clamp upper portion.

* * * * *